United States Patent
Eidenschink (10) Patent No.: US 9,480,561 B2
(45) Date of Patent: Nov. 1, 2016

(54) APPARATUS AND METHOD FOR AORTIC PROTECTION AND TAVI PLANAR ALIGNMENT

(71) Applicant: St. Jude Medical, Cardiology Division, Inc., St. Paul, MN (US)

(72) Inventor: Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 39 days.

(21) Appl. No.: 13/783,973

(22) Filed: Mar. 4, 2013

(65) Prior Publication Data
US 2013/0345796 A1    Dec. 26, 2013

Related U.S. Application Data

(60) Provisional application No. 61/664,408, filed on Jun. 26, 2012, provisional application No. 61/676,703, filed on Jul. 27, 2012.

(51) Int. Cl.
*A61F 2/24* (2006.01)
*A61F 2/01* (2006.01)
(Continued)

(52) U.S. Cl.
CPC ......... *A61F 2/2427* (2013.01); *A61B 17/1204* (2013.01); *A61B 17/12036* (2013.01);
(Continued)

(58) Field of Classification Search
CPC .... A61F 2/2427; A61F 2/243; A61F 2/2436; A61F 2/2433; A61F 2/013; A61F 2/0063; A61F 2002/0072; A61F 2002/0068; A61B 17/12022; A61B 17/12031; A61B 17/12036; A61B 17/1204; A61B 17/12131; A61B 17/12136; A61B 17/12109; A61B 17/12168; A61B 17/12172; A61B 2017/1205; A61B 17/221; A61B 2017/2217; A61B 2017/32056; A61B 2017/32016; A61B 17/0057; A61M 25/1002; A61M 25/10; A61M 2025/1047; A61M 2025/1072; A61M 1/1072; A61M 25/104; A61M 2025/1042; A61M 2025/1052; A61M 2025/1059; A61M 2025/1061; A61M 2025/1065; A61M 2025/109; A61M 2025/1095
USPC ............ 623/2.11, 1.2, 1.13, 1.15, 1.16, 1.11; 606/200, 159, 190–192, 194–195, 198, 606/153, 108, 151; 600/585; 604/523, 604/96.01, 102.01, 103.05, 103.07–103.09, 604/103.12, 104–106, 95.03
See application file for complete search history.

(56) References Cited

U.S. PATENT DOCUMENTS 4,423,730 A    1/1984    Gabbay
4,471,777 A    9/1984    McCorkle, Jr.
(Continued)

FOREIGN PATENT DOCUMENTS

DE    102004062296 A1    7/2006
EP        1129744 A1        9/2001
(Continued)

OTHER PUBLICATIONS

International Search Report and Written Opinion for Application No. PCt/US2011/001218 dated Nov. 11, 2011.
(Continued)

*Primary Examiner* — Jocelin Tanner
(74) *Attorney, Agent, or Firm* — Lerner, David, Littenberg, Krumholz & Mentlik, LLP (57) ABSTRACT

An assembly for guiding a medical apparatus within a patient includes an elongated shaft and a balloon affixed to the shaft and movable between a collapsed condition and an expanded condition. A mesh material may be affixed to the shaft and movable between a collapsed condition and an expanded condition. The balloon may project away from the shaft when the balloon is in the expanded condition. The mesh material may project away from the shaft when the mesh material is in the expanded condition.

15 Claims, 6 Drawing Sheets

(51) Int. Cl.
*A61B 17/12* (2006.01)
*A61M 25/10* (2013.01)

(52) U.S. Cl.
CPC ... *A61B17/12109* (2013.01); *A61B 17/12136* (2013.01); *A61B 17/12172* (2013.01); *A61F 2/013* (2013.01); *A61M 25/1002* (2013.01); *A61F 2230/0069* (2013.01); *A61M 2025/1047* (2013.01); *A61M 2025/1072* (2013.01); *A61M 2025/1086* (2013.01)

(56) References Cited

U.S. PATENT DOCUMENTS

| | | | |
|---|---|---|---|
| 4,546,759 A * | 10/1985 | Solar | 600/18 |
| 4,575,371 A * | 3/1986 | Nordqvist et al. | 604/103.07 |
| 5,090,958 A * | 2/1992 | Sahota | 604/98.01 |
| 5,120,299 A | 6/1992 | Lombardi | |
| 5,334,160 A | 8/1994 | Ellis | |
| 5,411,552 A | 5/1995 | Andersen et al. | |
| 5,733,325 A | 3/1998 | Robinson et al. | |
| 5,795,325 A * | 8/1998 | Valley et al. | 604/509 |
| 5,797,952 A | 8/1998 | Klein | |
| 5,827,324 A * | 10/1998 | Cassell et al. | 606/200 |
| 5,868,706 A * | 2/1999 | Cox | 604/96.01 |
| 5,924,424 A | 7/1999 | Stevens et al. | |
| 5,968,068 A | 10/1999 | Dehdashtian et al. | |
| 6,077,295 A | 6/2000 | Limon et al. | |
| 6,190,357 B1 * | 2/2001 | Ferrari et al. | 604/102.01 |
| 6,214,036 B1 | 4/2001 | Letendre et al. | |
| 6,231,588 B1 * | 5/2001 | Zadno-Azizi | 606/200 |
| 6,306,141 B1 | 10/2001 | Jervis | |
| 6,312,407 B1 * | 11/2001 | Zadno-Azizi | A61B 17/12022 604/103.03 |
| 6,361,545 B1 * | 3/2002 | Macoviak et al. | 606/200 |
| 6,375,668 B1 * | 4/2002 | Gifford et al. | 606/200 |
| 6,482,228 B1 | 11/2002 | Norred | |
| 6,607,551 B1 | 8/2003 | Sullivan et al. | |
| 6,623,518 B2 | 9/2003 | Thompson et al. | |
| 6,776,791 B1 | 8/2004 | Stallings et al. | |
| 8,414,644 B2 | 4/2013 | Quadri et al. | |
| 8,608,792 B2 | 12/2013 | Silveira et al. | |
| 2002/0120323 A1 | 8/2002 | Thompson et al. | |
| 2003/0014007 A1 * | 1/2003 | Eidenschink | A61M 25/104 604/96.01 |
| 2003/0023265 A1 | 1/2003 | Forber | |
| 2003/0199963 A1 | 10/2003 | Tower et al. | |
| 2004/0087900 A1 | 5/2004 | Thompson et al. | |
| 2004/0093063 A1 | 5/2004 | Wright et al. | |
| 2004/0204749 A1 | 10/2004 | Gunderson | |
| 2004/0236406 A1 | 11/2004 | Gregorich | |
| 2004/0267346 A1 | 12/2004 | Shelso | |
| 2004/0267348 A1 | 12/2004 | Gunderson et al. | |
| 2005/0020974 A1 | 1/2005 | Noriega et al. | |
| 2005/0027345 A1 | 2/2005 | Horan et al. | |
| 2005/0033398 A1 | 2/2005 | Seguin | |
| 2005/0049667 A1 | 3/2005 | Arbefeuille et al. | |
| 2005/0049674 A1 | 3/2005 | Berra et al. | |
| 2005/0065590 A1 | 3/2005 | Shelso | |
| 2005/0222662 A1 | 10/2005 | Thompson et al. | |
| 2006/0058865 A1 | 3/2006 | Case et al. | |
| 2006/0100688 A1 | 5/2006 | Jordan et al. | |
| 2006/0106415 A1 | 5/2006 | Gabbay | |
| 2006/0111771 A1 | 5/2006 | Ton et al. | |
| 2006/0142848 A1 | 6/2006 | Gabbay | |
| 2006/0149294 A1 | 7/2006 | Argentine et al. | |
| 2006/0167468 A1 | 7/2006 | Gabbay | |
| 2006/0195184 A1 | 8/2006 | Lane et al. | |
| 2006/0259120 A1 | 11/2006 | Vongphakdy et al. | |
| 2006/0276872 A1 | 12/2006 | Arbefeuille et al. | |
| 2007/0027534 A1 | 2/2007 | Bergheim et al. | |
| 2007/0073391 A1 | 3/2007 | Bourang et al. | |
| 2007/0088431 A1 | 4/2007 | Bourang et al. | |
| 2007/0106364 A1 | 5/2007 | Buzzard et al. | |
| 2007/0112422 A1 | 5/2007 | Dehdashtian | |
| 2007/0142858 A1 * | 6/2007 | Bates | 606/200 |
| 2007/0162100 A1 | 7/2007 | Gabbay | |
| 2007/0168013 A1 | 7/2007 | Douglas | |
| 2007/0203561 A1 | 8/2007 | Forster et al. | |
| 2007/0203575 A1 | 8/2007 | Forster et al. | |
| 2007/0233224 A1 | 10/2007 | Leynov et al. | |
| 2007/0239271 A1 | 10/2007 | Nguyen | |
| 2007/0293930 A1 | 12/2007 | Wang et al. | |
| 2008/0103443 A1 * | 5/2008 | Kabrick et al. | 604/103.07 |
| 2008/0114443 A1 | 5/2008 | Mitchell et al. | |
| 2008/0147182 A1 | 6/2008 | Righini et al. | |
| 2008/0221666 A1 | 9/2008 | Licata et al. | |
| 2008/0228255 A1 | 9/2008 | Rust et al. | |
| 2008/0255662 A1 | 10/2008 | Stacchino et al. | |
| 2008/0262590 A1 | 10/2008 | Murray | |
| 2008/0319526 A1 | 12/2008 | Hill et al. | |
| 2009/0054975 A1 | 2/2009 | del Nido et al. | |
| 2009/0143851 A1 | 6/2009 | Paul, Jr. | |
| 2009/0204197 A1 | 8/2009 | Dorn et al. | |
| 2009/0222035 A1 * | 9/2009 | Schneiderman | 606/200 |
| 2009/0228093 A1 | 9/2009 | Taylor et al. | |
| 2009/0276027 A1 | 11/2009 | Glynn | |
| 2009/0281610 A1 | 11/2009 | Parker | |
| 2009/0287290 A1 | 11/2009 | Macaulay et al. | |
| 2010/0070015 A1 | 3/2010 | Schneider et al. | |
| 2010/0131039 A1 | 5/2010 | Chau et al. | |
| 2010/0145438 A1 | 6/2010 | Barone | |
| 2010/0152834 A1 | 6/2010 | Hannes et al. | |
| 2010/0268315 A1 | 10/2010 | Glynn et al. | |
| 2010/0312325 A1 | 12/2010 | Dorn | |
| 2011/0029065 A1 | 2/2011 | Wood et al. | |
| 2011/0077731 A1 | 3/2011 | Lee et al. | |
| 2011/0078350 A1 | 3/2011 | Carls | |
| 2011/0098805 A1 | 4/2011 | Dwork et al. | |
| 2011/0137401 A1 | 6/2011 | Dorn et al. | |
| 2011/0172764 A1 | 7/2011 | Badhwar | |
| 2011/0224678 A1 | 9/2011 | Gabbay | |
| 2011/0251666 A1 | 10/2011 | Schmitt et al. | |
| 2011/0251679 A1 | 10/2011 | Wiemeyer et al. | |
| 2011/0257720 A1 | 10/2011 | Peterson et al. | |
| 2011/0264201 A1 * | 10/2011 | Yeung | A61F 2/2418 623/2.11 |
| 2011/0264202 A1 | 10/2011 | Murray, III et al. | |
| 2011/0288636 A1 | 11/2011 | Rolando et al. | |
| 2011/0301685 A1 | 12/2011 | Kao | |
| 2012/0078350 A1 | 3/2012 | Wang et al. | |
| 2012/0123528 A1 | 5/2012 | Knippel et al. | |
| 2013/0131775 A1 | 5/2013 | Hadley et al. | |
| 2013/0204344 A1 | 8/2013 | Tatalovich et al. | |
| 2013/0274860 A1 | 10/2013 | Argentine | |

FOREIGN PATENT DOCUMENTS

| | | |
|---|---|---|
| EP | 1157673 A2 | 11/2001 |
| WO | 9620025 A1 | 7/1996 |
| WO | 9748343 A1 | 12/1997 |
| WO | 9965418 A1 | 12/1999 |
| WO | 2006069704 A2 | 7/2006 |
| WO | 2006124549 A1 | 11/2006 |
| WO | 2007002863 A2 | 1/2007 |
| WO | 2007134290 A2 | 11/2007 |
| WO | 2008031103 A2 | 3/2008 |
| WO | 2008097556 A1 | 8/2008 |
| WO | 2009062955 A1 | 5/2009 |
| WO | 2009/091509 A1 | 7/2009 |
| WO | 2009108942 A1 | 9/2009 |
| WO | 2010005524 A2 | 1/2010 |
| WO | 2010022138 A2 | 2/2010 |
| WO | 2010051025 A1 | 5/2010 |
| WO | 2010087975 A1 | 8/2010 |
| WO | 2011025945 A1 | 3/2011 |
| WO | 2012036740 A2 | 3/2012 |

OTHER PUBLICATIONS

International Search Report and Written Opinion for Application No. PCT/US2012/047283 dated Oct. 30, 2012.

(56) References Cited

OTHER PUBLICATIONS

International Search Report dated Feb. 2, 2012 for Application No. PCT/US2011/001446.
International Search Report for Application No. PCY/US2011/001596 dated May 8, 2012.
International Search Report and Written Opinion for Application No. PCT/US2013/047891 dated Dec. 4, 2013.
International Search Report and Written Opinion for Application No. PCT/US2013/048413 dated Dec. 4, 2013.
Japanese Office Action for Application No. 2013-519648 dated Jun. 30, 2015.

* cited by examiner

APPARATUS AND METHOD FOR AORTIC PROTECTION AND TAVI PLANAR ALIGNMENT

CROSS-REFERENCE TO RELATED APPLICATIONS

This application claims the benefit of the filing date of U.S. Provisional Patent Application Nos. 61/664,408 filed Jun. 26, 2012, and 61/676,703 filed Jul. 27, 2012, the disclosures of which are hereby incorporated herein by reference.

BACKGROUND OF THE INVENTION

The present invention is related to heart valve replacement, and more particularly to devices, systems, and methods for transcatheter delivery of collapsible prosthetic heart valves.

Prosthetic heart valves that are collapsible to a relatively small circumferential size may be delivered into a patient less invasively than valves that are not collapsible. For example, a collapsible valve may be delivered into a patient via a tube-like delivery apparatus such as a catheter, a trocar, a laparoscopic instrument, or the like. This collapsibility may avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such a valve into a delivery apparatus and ultimately into a patient, the valve must first be collapsed or crimped to reduce its circumferential size. For example, a conventional collapsible prosthetic valve is typically collapsed and retained in a collapsed state by a sheath for delivery into the patient, for example, through a femoral artery.

When a collapsed prosthetic valve has reached the desired implant site in the patient (e.g., at or near the annulus of the patient's heart valve that is to be replaced by the prosthetic valve), the prosthetic valve may be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically begins to expand as the sheath covering the valve is withdrawn.

Figure 1:
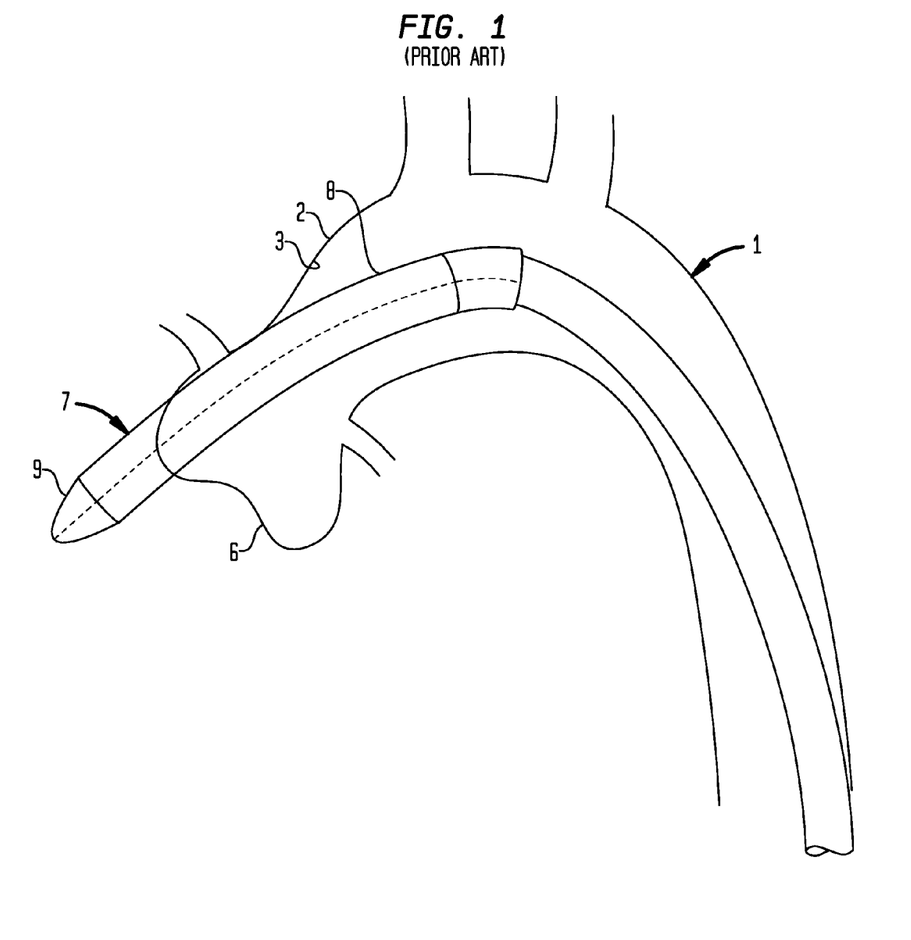
FIG. 1 is a diagrammatic view showing the use of a conventional transfemoral delivery device to deliver a collapsible prosthetic heart valve to the aortic valve annulus.

Despite the various improvements that have been made to the collapsible prosthetic heart valve delivery process, conventional delivery devices, systems, and methods suffer from some shortcomings. For example, in conventional delivery devices for collapsible prosthetic valves such as the device 7 shown in FIG. 1, it may be difficult to control the alignment of the longitudinal axis of the distal sheath 8 relative to the geometric center of the native annulus 6 (i.e., planar alignment). During use of the device 7 to deliver a prosthetic valve to the native annulus 6, the distal tip 9 of the device may contact and stretch the inner wall 3 of the aortic arch 2, which may cause damage to the inner wall. Even if a steerable device 7 is used, it may be difficult to move the distal sheath 8 through the tight radius of the aortic arch 2 without contacting and stretching the inner wall 3. Also, during use of the device 7 for delivery of a prosthetic valve, calcified particles may be detached from the native valve or the inner wall 3 of the aorta 1, thereby forming emboli that may travel within the vascular system and cause a stroke or other vascular occlusion.

There therefore is a need for further improvements to the devices, systems, and methods for transcatheter delivery of collapsible prosthetic heart valves. Among other advantages, the present invention may address one or more of these needs.

BRIEF SUMMARY OF THE INVENTION

An assembly for guiding a medical apparatus within a patient and a method of guiding a medical apparatus within a patient are disclosed. An assembly for guiding a medical apparatus within a patient includes an elongated shaft and a balloon affixed to the shaft and movable between a collapsed condition and an expanded condition, the balloon projecting away from the shaft in the expanded condition.

The shaft may include a lumen extending longitudinally therethrough, the lumen being adapted to receive a catheter. The shaft may have an elliptical cross section. The balloon may include two lobes extending in substantially opposite radial directions from the shaft. The shaft may include at least one inflation lumen extending between a proximal end of the shaft and the balloon. The balloon may include a plurality of compartments disposed adjacent to one another in a length direction of the shaft. Each of the plurality of compartments may be in fluid communication with an inflation lumen.

The assembly may also include a mesh material affixed to the shaft and movable between a collapsed condition and an expanded condition, the mesh material projecting away from the shaft in the expanded condition. The mesh material may include two wings extending in substantially opposite radial directions from the shaft. The mesh material may be positioned on the shaft proximally of the balloon. A distal end of the mesh material may be attached to a proximal end of the balloon. The mesh material may include at least one stiffening wire biased to a straight shape. The assembly may also include comprising an elongated sheath surrounding a portion of the shaft, the sheath being slidable longitudinally along the shaft, wherein the mesh material is adapted to be collapsed inside the sheath when in the collapsed condition.

The balloon may have a cylindrical shape and an aperture extending therethrough along a balloon axis that is substantially parallel to a longitudinal axis of the shaft. The aperture may be spaced apart from the shaft in a radial direction of the shaft. The assembly may also include a mesh material affixed to the shaft and movable between a collapsed condition and an expanded condition, the mesh material projecting away from the shaft in the expanded condition, the mesh material including a cylindrical shape and an aperture extending therethrough along a mesh material axis that is substantially parallel to the longitudinal axis of the shaft. The balloon axis and the mesh material axis may be coincident.

An assembly for guiding a medical apparatus within a patient includes an elongated shaft having a lumen extending longitudinally therethrough, an elongated sheath surrounding a portion of the shaft, and a mesh material affixed to the shaft and movable between a collapsed condition and an expanded condition. The lumen may be adapted to receive an elongated medical apparatus extending therethrough. The sheath may be slidable longitudinally along the shaft. The mesh material may project away from the shaft in the expanded condition. The mesh material may be adapted to be collapsed inside the sheath when in the collapsed condition.

The mesh material may include two wings extending in substantially opposite radial directions from the shaft. The mesh material may include at least one stiffening wire biased to a straight shape. The mesh material may include a cylindrical shape and an aperture extending therethrough along a mesh material axis that is substantially parallel to a longitudinal axis of the shaft.

A method of guiding a medical apparatus within a patient includes inserting an elongated catheter assembly to a position within the aorta of a patient, the catheter assembly including an elongated shaft and a balloon affixed to the shaft, and inflating the balloon to move it from a collapsed condition to an expanded condition, the balloon projecting away from the shaft.

The method may also include inserting an elongated pigtail catheter into the aorta through a lumen of the elongated shaft. The step of inflating the balloon may include flowing a fluid into the balloon through at least one lumen extending from a proximal end of the shaft to the balloon. After the balloon is inflated, a first outer surface of the balloon may be disposed adjacent an inner wall of the aorta. The method may also include inserting a prosthetic valve delivery device into the aorta such that a distal sheath of the delivery device contacts a second outer surface of the balloon. The second outer surface of the balloon may be located opposite the first outer surface of the balloon. The second outer surface of the balloon may be defined around an aperture extending through the balloon along a balloon axis that is substantially parallel to a longitudinal axis of the shaft.

The catheter assembly may also include a mesh material affixed to the shaft, the method further including deploying the mesh material to move it from a collapsed condition to an expanded condition, the mesh material projecting away from the shaft. After the mesh material is deployed, the mesh material may extend across openings from the aorta to at least one of the great vessels. The step of deploying the mesh material may include sliding an elongated sheath partially surrounding the shaft in a proximal direction relative to the shaft along a longitudinal axis of the shaft. The method may also include inserting a prosthetic valve delivery device into the aorta such that at least a portion of a distal sheath of the delivery device passes through an aperture extending through the mesh material along a mesh material axis that is substantially parallel to the longitudinal axis of the shaft.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) of the disclosed delivery devices. "Proximal" is to be understood as relatively close to the user and "distal" is to be understood as relatively farther away from the user.

Referring to FIG. 2A-2D, an exemplary delivery assistance device 10 includes an elongated shaft 20 having a proximal end (not shown) and a distal end 12. The shaft 20 may have an elliptical or oval cross-section with the longer dimension H extending between one side 22 and another side 24 of the shaft and the shorter dimension W extending substantially perpendicular to the long dimension H. A lumen 28 extending longitudinally through the shaft 20 is adapted to receive an elongated medical apparatus, shown for example as a pigtail catheter 11 (FIG. 3A), the purpose of which will be described below.

Figure 2A:
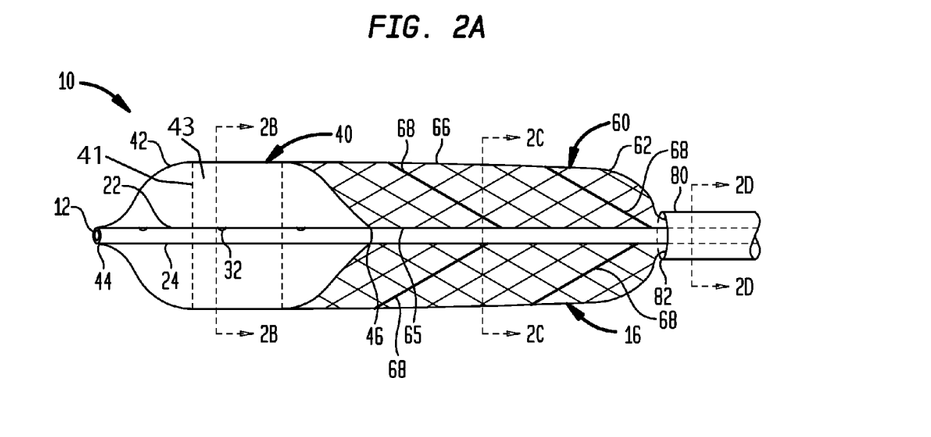
FIG. 2A is a highly schematic side elevational view of a delivery assistance device for a collapsible prosthetic heart valve according to a first embodiment of the invention, shown in partial cross-section and in the deployed condition.
Figure 2B:
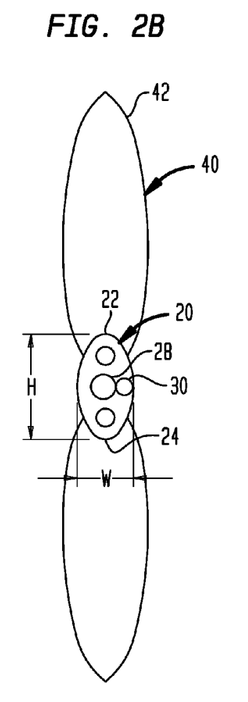
FIG. 2B is a highly schematic cross-sectional view of the device of FIG. 2A, taken along line 2B-2B of FIG. 2A.

An inflatable balloon 40 is connected to the shaft 20 so that its distal end 44 is coterminous with the distal end 12 of the shaft, and its proximal end 46 is spaced proximally therefrom. The balloon 40 has two lobes 42 that project away from the respective sides 22 and 24 of the shaft 20 in substantially opposite directions. As shown in FIG. 2B, the lobes 42 are not in fluid communication with one another.

Figure 2C:
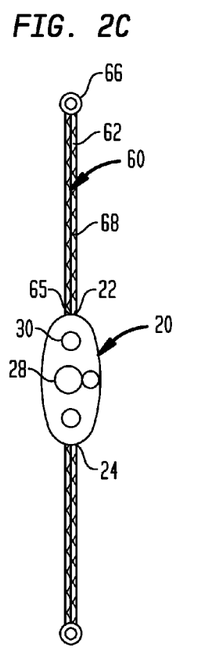
FIG. 2C is a highly schematic cross-sectional view of the device of FIG. 2A, taken along line 2C-2C of FIG. 2A.
Figure 2D:
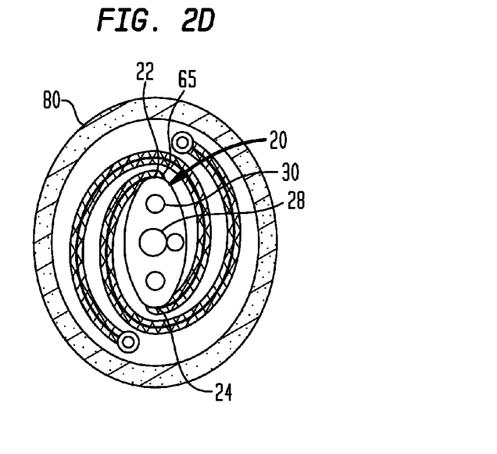
FIG. 2D is a highly schematic cross-sectional view of the device of FIG. 2A, taken along line 2D-2D of FIG. 2A.

However, it will be appreciated that the lobes 42 may be in fluid communication with one another, as will be described below in connection with FIG. 6A. One or more inflation lumens 30 extend longitudinally through the shaft 20 for inflating the balloon 40. Each inflation lumen 30 extends from the proximal end of the shaft 20 where it connects to an inflation source, to an opening 32 through a sidewall of the shaft that is in fluid communication with the interior of one of lobes 42. Although FIGS. 2B, 2C, and 2D show the shaft 20 having three inflation lumens 30, any number of inflation lumens needed to inflate the balloon 40 and each of the lobes 42 thereof may be provided. As shown in FIG. 2A, the balloon 40 can include septums 41 that can divide adjacent balloon compartments 43 from one another in the longitudinal or length direction of the shaft. As illustrated in FIG. 2A, each of the compartments 43 can be in fluid communication with one of the inflation lumens 32.

The elliptical cross-section of the shaft 20 may enable it to bend readily along the short dimension W but not to bend easily along the long dimension H. However, the elliptical cross-section may provide the shaft 20 with sufficient cross-sectional area to accommodate the lumens 28 and 30 while permitting preferential bending of the shaft to make it easier to maneuver the delivery assistance device 10 through the aortic arch 2.

Proximally of the balloon 40, the shaft 20 may include a mesh material in the form of a fiber mesh 60. Although the mesh material is shown in the figures as a fiber mesh 60, the mesh material may be made of various material and have various forms, including, for example, a polymer sheet with holes, a woven polymer, and woven nitinol, among others. The fiber mesh 60 may have two wings 62, one connected to side 22 of the shaft 20, and the other connected to side 24 of the shaft. Each wing 62 may have one longitudinal edge 65 connected to the shaft 20 and a free longitudinal edge 66 that extends substantially parallel to the shaft for at least a portion of the wing. The longitudinal edges 65 may be connected to the shaft 20 substantially continuously along the shaft from the proximal end 46 of the balloon 40 to the proximal end of the fiber mesh 60, or at spaced positions there along.

At least one stiffening wire 68 extends from the shaft 20 to the free edge 66 of each wing 62. Preferably, each wing 62 includes plural stiffening wires 68 spaced along its length. The stiffening wires 68 may be oriented at an oblique angle relative to the shaft 20, with the ends of the stiffening wires adjacent the free edges 66 of the wings 62 being located distally relative to the ends of the stiffening wires adjacent the shaft. The stiffening wires 68 may be made, for example, from a memory metal such as nitinol, and may be biased to a straight shape when the wings 62 are deployed, as described below.

The wings 62 are movable between an initial collapsed condition and a deployed condition. In the collapsed condition, the wings 62 may assume any configuration, but preferably are initially wrapped around the shaft 20, with each wing preferably being wrapped around both sides 22, 24 of the shaft. In the deployed condition, the wings 62 may project away from the respective sides 22 and 24 of the shaft 20 in substantially opposite directions.

An elongated sheath 80 may be assembled on the shaft 20 so as to be longitudinally slidable between open and closed conditions. In the closed condition, the sheath 80 is in a distal-most position covering the fiber mesh 60, with the distal end 82 of the sheath abutting the proximal end 46 of the balloon 40. In the fully open condition, the sheath 80 is in a proximal-most position with the distal end 82 of the sheath spaced from the proximal end 46 of the balloon 40 to expose a major portion of the fiber mesh 60 while still covering a proximal portion thereof.

Figure 3A:
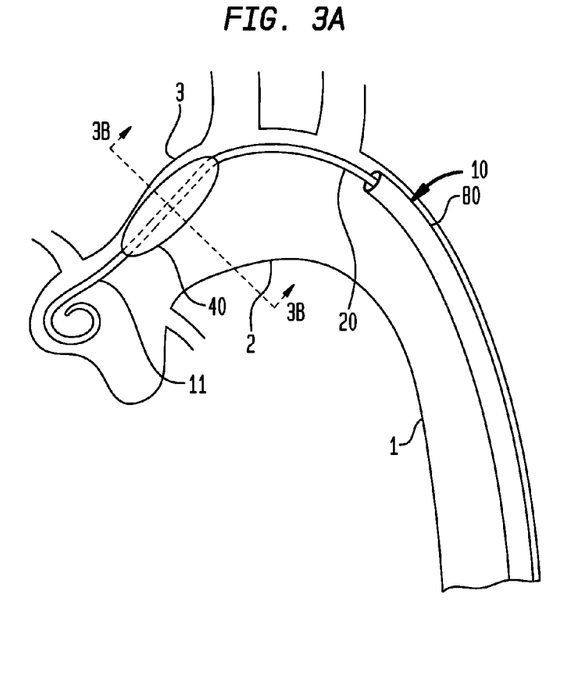
FIG. 3A is a diagrammatic view showing the device of FIG. 2A, without the fiber mesh, positioned in an aortic arch.
Figure 5:
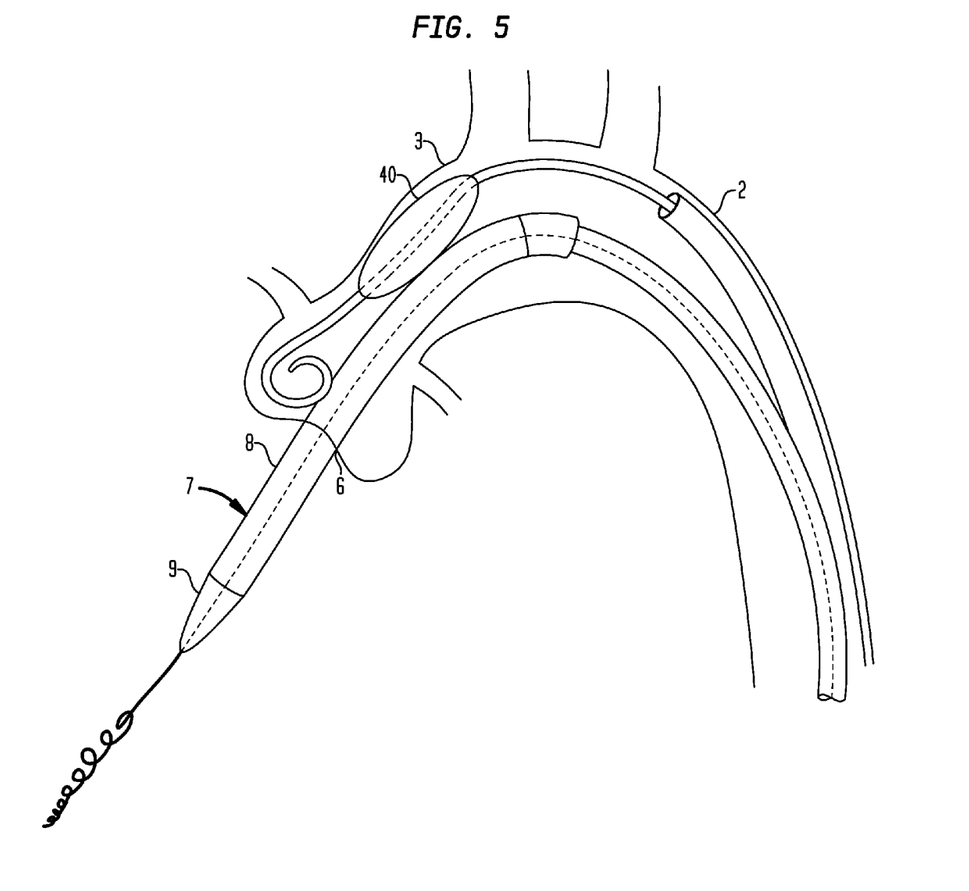
FIG. 5 is a diagrammatic view showing the device of FIG. 2A positioned in an aortic arch with a transfemoral delivery device for a collapsible prosthetic heart valve.

The following will describe the use of the delivery assistance device 10 during the placement of a collapsible prosthetic heart valve. Referring to FIG. 3A, the delivery assistance device 10 may be inserted with the balloon 40 in a deflated condition, into the aorta 1 of a patient, for example, through the femoral artery, although other delivery approaches are contemplated herein. The device 10 may be inserted into the aorta 1 with a pigtail catheter 11 extending through the lumen 28 of the shaft 20. The pigtail catheter 11 may be used for injecting a die into the aorta to assist in the visualization of the prosthetic heart valve or the prosthetic valve delivery device 7 (FIG. 5) during deployment of the valve. The device 10 may be pushed distally through the aorta until the balloon 40 thereof is at the location within the aortic arch 2 at which it is anticipated there will be contact between the balloon and the prosthetic valve delivery device 7.

Figure 3B:
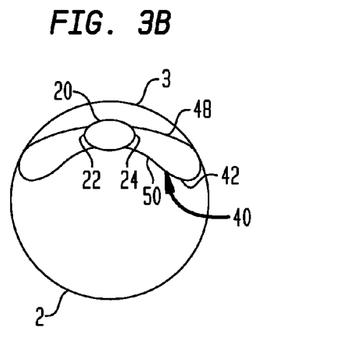
FIG. 3B is a diagrammatic cross-sectional view taken along line 3B-3B of FIG. 3A.

Thereafter, the lobes 42 of the balloon 40 may be inflated, for example, by providing fluid flow through the inflation lumens 30 into the interior of the lobes. As shown in FIG. 3B, with the lobes 42 inflated, one surface 48 of each lobe may contact the inner surface of the outer radial wall 3 of the aortic arch 2, and the opposite surface 50 of each lobe may face towards the center of the aorta.

Figure 4A:
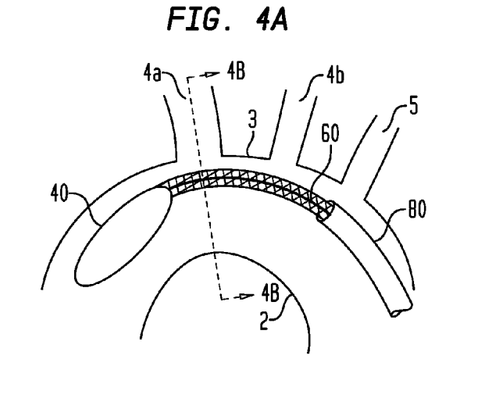
FIG. 4A is a diagrammatic view showing the device of FIG. 2A positioned in an aortic arch, with the fiber mesh in the deployed condition.

Referring to FIG. 4A, at any time after insertion of the device 10 into the aorta 1, the sheath 80 may be retracted proximally relative to the shaft 20 to uncover a portion of the two wings 62 of the fiber mesh 60. As the sheath 80 is retracted, each stiffening wire 68 may attempt to straighten because of the memory metal therein, thereby uncoiling the wings 62 from around the shaft 20.

Figure 4B:
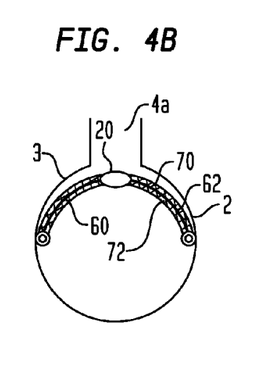
FIG. 4B is a diagrammatic cross-sectional view taken along line 4B-4B of FIG. 4A.

In the deployed condition, as shown in FIG. 4B, one surface 70 of each wing 62 may contact the inner surface of the outer radial wall 3 of the aortic arch 2, and the opposite surface 72 of each wing may face towards the center of the aorta. The wings 62 of the fiber mesh 60 may extend across, for example, the openings to two of the three great vessels branching off of the aortic arch 2, including the brachiocephallic artery 4a and the left common carotid artery 4b. By extending across the openings in the aortic arch 2 leading to one or more of the great vessels 4a and 4b, the fiber mesh 60 may prevent calcified particles that may become detached from the native valve or the aorta during deployment of the prosthetic heart valve from entering these great vessels.

The opening to the third great vessel, the left subclavian artery 5 (FIG. 4A), may also be covered by the fiber mesh 60, but covering that opening is not as great of a concern as covering the openings to the other two great vessels. The opening to the left subclavian artery is typically spaced farther away from the aortic annulus 6 than the openings to the other two great vessels, so covering opening to the left subclavian artery may require a longer fiber mesh 60. Moreover, having emboli enter the left subclavian artery is not as great of a concern as having emboli enter the other two great vessels. Also, the opening to the subclavian artery may need to remain uncovered so that the artery may be used as an insertion pathway through which the device 10 or the pigtail catheter 11 can reach the aortic arch 2.

The amount of the fiber mesh 60 that is deployed from the sheath 80 may be controlled by controlling the amount by which the sheath is retracted. How far the user may desire to retract the sheath 80 from the fiber mesh 60 may depend on the location of the openings to the great vessels 4a and 4b relative to the position of the device 10.

After inflation of the balloon 40 and deployment of the fiber mesh 60, a prosthetic valve delivery device 7 may be inserted, for example, through the femoral artery of the patient, and advanced distally through the aorta 1 towards the aortic annulus 6. As the delivery device 7 is advanced along the aortic arch 2, a distal tip 9 of the delivery device or a portion of the distal sheath 8 thereof may contact the balloon 40, thereby reducing the amount of contact between the distal sheath and the outer radial wall 3 of the aortic arch compared to delivery (e.g., FIG. 1B) without the use of the assistance device 10. Furthermore, the contact between the distal sheath 8 and the balloon 40 may orient the distal sheath generally along the centerline of the aortic arch 2 and direct it toward the geometric center of the of the aortic annulus 6.

Once the delivery device 7 has reached the proper position relative to the native aortic annulus 6, the distal sheath 8 may be retracted to deploy the prosthetic heart valve, and the delivery device may be withdrawn from the aorta 1. After withdrawal of the valve delivery device 7, the fiber mesh 60 of the device 10 may be moved to the collapsed condition (shown in FIG. 2D) by advancing the sheath 80 distally relative to the shaft 20. As the sheath 80 is advanced, the distal end 82 thereof may contact and bend the stiffening wires 68, thereby providing a radially-inward force to the fiber mesh 60. At any time after withdrawal of the valve delivery device 7 from the aorta 1, the balloon 40 may be deflated to the collapsed condition by withdrawing fluid from the lobes 42 through the inflation lumens 30. After the fiber mesh 60 and the balloon 40 have been moved to the collapsed condition, the assistance device 10 may be withdrawn from the aorta 1.

Figure 6A:
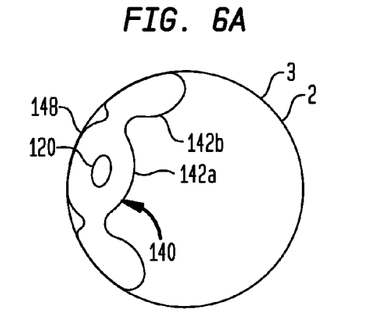
FIG. 6A is a diagrammatic cross-sectional view showing an alternate embodiment of the balloon portion of the device of FIG. 2A, positioned in an aorta.

Referring now to FIG. 6A, an alternate embodiment of a balloon 140 suitable for use in the assistance device 10 of FIG. 2A is shown. The balloon 140 has three lobes 142 including a lobe 142a surrounding the shaft 120, and two outer lobes 142b extending from opposite sides of the lobe. The three lobes 142 may communicate internally with one another so as to provide the balloon 140 with a continuous interior. The balloon 140 may be inflated by providing fluid flow through one or more inflation lumens such as the inflation lumens 30 (FIG. 2B) and through one or more openings 32. Any appropriate fluid known in the art may be used to inflate the balloon 140, including, for example, a saline contrast mixture or a gas. Since the interiors of the lobes 142 communicate with one another, all three lobes may be inflated and deflated through a single inflation lumen 30 and opening 32. However, inflation and deflation may be accomplished mere quickly with a plurality of inflation lumens and openings.

When the balloon 140 is inserted into the aortic arch 2 and inflated, one surface 148 of each of the three lobes 142 may contact the inner surface of the outer radial wall 3 of the aortic arch 2, such that the lobes may collectively at least partially conform to the contour of the outer radial wall of the aortic arch.

Figure 6B:
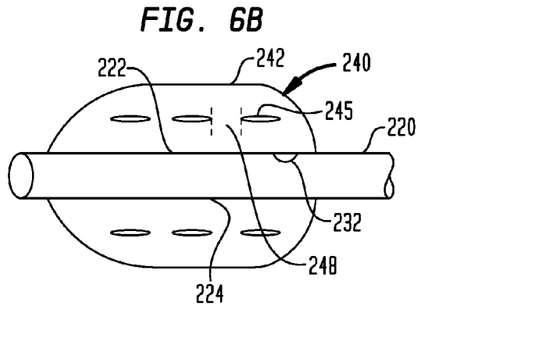
FIG. 6B is an enlarged highly schematic side elevational view showing another embodiment of the balloon portion of the device of FIG. 2A.

FIG. 6B illustrates another alternate embodiment of a balloon 240 suitable for use in the assistance device 10 of FIG. 2A. The balloon 240 has two lobes 242 extending from the shaft 220, each lobe extending from a respective side 222 and 224 of the shaft. Each lobe 242 includes a plurality of stitches 245 positioned substantially in the middle of the lobe and oriented substantially parallel to the longitudinal axis of the shaft 220. Each stitch 245 joins opposing sides of the lobe 242 to one another, the ends of the stitches being spaced apart to create channels 248 within the interior of the lobe.

The balloon 240 may be inflated in the same manner as the balloons 40 and 140 described above. When the balloon 240 is inflated, the stitches 245 will keep the opposing sides of each lobe 242 closer together than the opposing sides of the balloon 40. As the balloon 240 is thinner than the balloons described above, it may more readily bend around the shaft 220 and more easily conform to the contour of the outer radial wall 3 of the aortic arch 2.

Figure 7A:
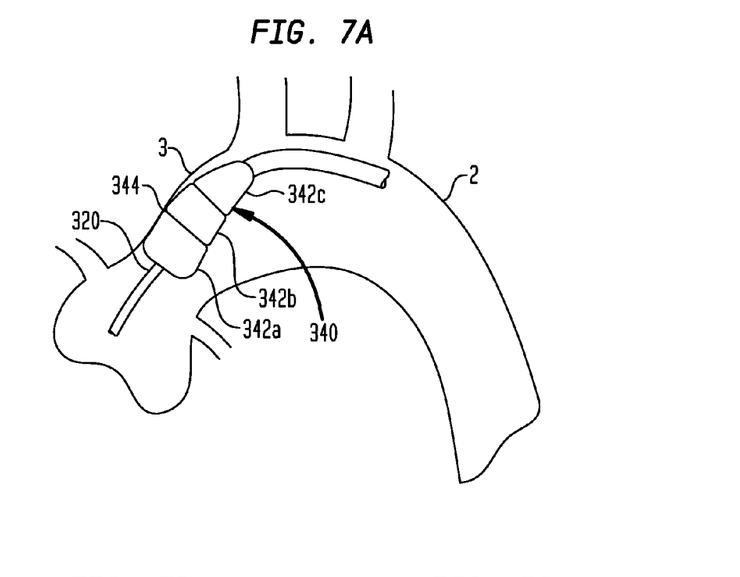
FIG. 7A is a diagrammatic view showing a further embodiment of the balloon portion of the device of FIG. 2A, shown in an aorta.

Referring now to FIG. 7A, yet another embodiment of a balloon 340 suitable for use in the assistance device 10 of FIG. 2A is shown. The balloon 340 may have three compartments 342 surrounding the shaft 320 and arranged adjacent one another in the length direction of the shaft. The three compartments 342 may include a distal compartment 342a, a medial compartment 342b, and a proximal compartment 342c. The interior of each compartment may be separated from the interiors of the other compartments by septums 344. Each septum 344 is disposed between adjacent compartments and may extend radially outward from the shaft 320 in a plane substantially perpendicular to the longitudinal axis of the shaft.

Each of the three compartments 342 may be independently inflated by providing fluid flow through a corresponding inflation lumen such as the inflation lumen 30 (FIG. 2B). The user can chose a separate degree of inflation for each of the compartments 342 to achieve a desired shape of the balloon 340. For example, as shown in FIG. 7A, the distal compartment 342a can be inflated the most, the medial compartment 342b can be inflated less, and the proximal compartment 342c can be inflated the least. Such independent inflation of the compartments 342 enables the user to control the shape of the balloon 340 to conform to the contour of the outer radial wall 3 of the aortic arch 2, or to provide a desired balloon shape facing the center of the aortic arch for guiding a delivery device, such as the valve delivery device 7, through the aortic arch toward the nature valve annulus.

Figure 7B:
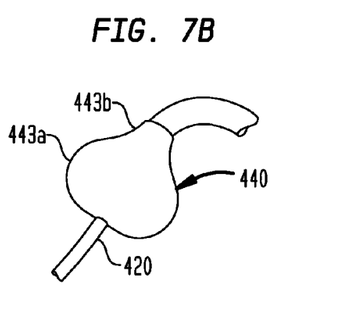
FIGS. 7B and 7C are highly schematic side elevational views showing still other embodiments of the balloon portion of the device of FIG. 2A.

Referring now to FIG. 7B, a still further embodiment of a balloon 440 suitable for use in the assistance device 10 of FIG. 2A is shown. The balloon 440 forms a single compartment surrounding the shaft 420. The balloon 440 is formed so that a distal portion 443a of the balloon has one degree of compliancy and a proximal portion 443b of the balloon has another degree of compliancy. In such an embodiment, the user can determine the shape of the balloon to some extent, depending on the degree to which the balloon is inflated.

In FIG. 7B, the distal portion 443a of the balloon 440 may be more compliant under a given internal pressure, so that when the internal pressure is low, both portions 443a and 443b may have the same shape, but when the internal pressure is high, the distal portion 443a may extend further away from the shaft 420 than the proximal portion 443b, giving the balloon a pear shape.

Figure 7C:
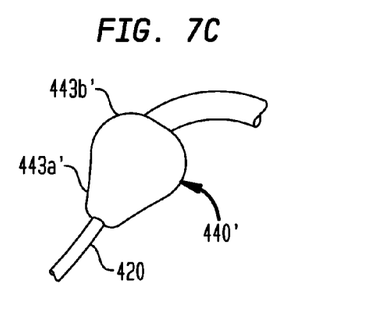

Alternatively, in FIG. 7C, the distal portion 443a' of the balloon 440' may be less compliant under a given internal pressure, so that when the internal pressure is low, both portions 443a' and 443b' may have the same shape, but when the internal pressure is high, the proximal portion 443b' may extend further away from the shaft 420 than the distal portion 443a', giving the balloon a pear shape opposite the pear shape shown in FIG. 7B.

Figures 8A, 8B:
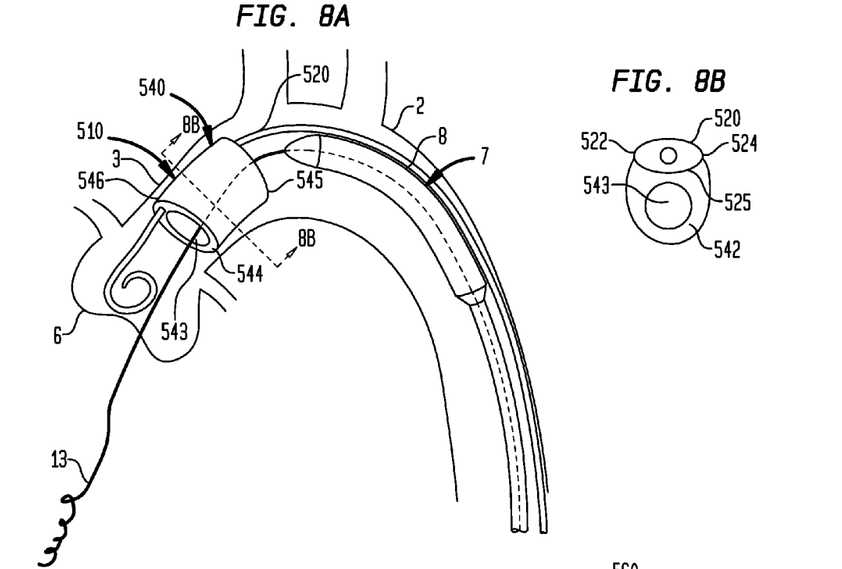
FIG. 8A is a diagrammatic view showing a delivery assistance device for a collapsible prosthetic heart valve according to another embodiment of the invention, positioned in an aortic arch with a transfemoral delivery device for a collapsible prosthetic heart valve.
FIG. 8B is a diagrammatic cross-sectional view of the device of FIG. 8A, taken along line 8B-8B of FIG. 8A.

FIGS. 8A and 8B illustrate an alternate embodiment of an assistance device 510 that is substantially the same as the assistance device 10 shown in FIG. 2A, except that it includes a balloon 540 having a hollow cylindrical shape. The device 510 includes a shaft 520 which may be similar to the shafts described above. Thus, the shaft 520 may have an elliptical or oval cross-section with the longer dimension extending between one side 522 and another side 524 of the shaft. The balloon 540 maybe attached to a surface 525 of the shaft 520 extending between sides 522 and 524.

The balloon 540 has a cylindrical outer surface and a cylindrical inner surface defining a channel 543 extending between a distal surface 544 and a proximal surface 545 of the balloon, thereby defining a balloon having a single annular compartment 542. The longitudinal axis of the balloon 540 preferably is substantially parallel to the longitudinal axis of the shaft 520. The channel 543 is sized to accommodate the insertion therethrough of the distal sheath 8 of the prosthetic valve delivery device 7. The size of the balloon 540 and the location of the channel 543 may be designed such that the centerline of a typical aortic arch 2 will extend through the channel when the device 510 is inserted into the aortic arch. For ease of maneuvering the distal sheath 8 into the channel 543 of the balloon 540, the proximal surface 545 of the balloon may have a chamfered edge leading into the channel, such that the channel may have a greater diameter at the proximal end of the balloon than at the distal end.

In use, the assistance device 510 is first inserted into the aortic arch 2, and the balloon 540 is inflated. Next, the distal sheath 8 of the valve delivery device 7 is inserted into the aortic arch 2 for delivery of a prosthetic valve to the aortic annulus 6 of the patient. While the distal sheath 8 is being advanced along the aortic arch 2, a portion of the distal sheath may extend through the channel 543 of the balloon 540, such that there may be a reduced amount of contact between the distal sheath and the outer radial wall 3 of the aortic arch compared to delivery (e.g., FIG. 1B) without the use of the assistance device 510. A user, such as an interventional cardiologist, may visualize the balloon 540 using x-rays, for example, so that a guide wire 13 extending through the distal sheath can be guided through the channel 543 of the balloon. Furthermore, as the distal sheath 8 passes through the channel 543 of the balloon 540, it may be oriented generally along the centerline of the aortic arch 2 and directed toward the geometric center of the aortic annulus 6.

Figure 8C:
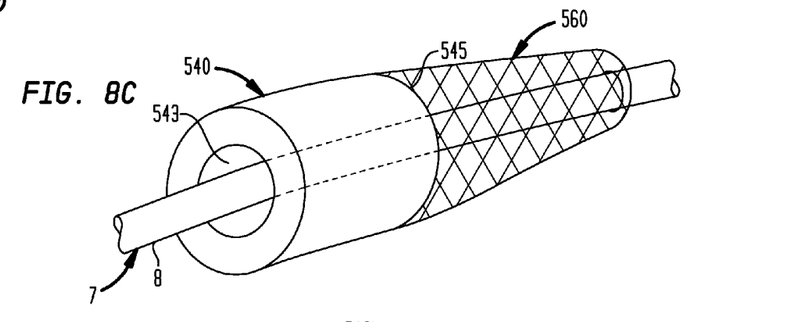
FIG. 8C is a highly schematic perspective view of a delivery assistance device for a collapsible prosthetic heart valve according to yet another embodiment of the invention, shown in partial cross-section and in the deployed condition.

FIG. 8C illustrates an embodiment of a mesh material in the form of a fiber mesh 560 suitable for use in the assistance device 510 of FIG. 8A. Although the mesh material is shown in FIG. 8C as a fiber mesh 560, the mesh material may be made of various material and have various forms, as described above with reference to the fiber mesh 60. The fiber mesh 560 may have a frusto-conical shape that extends proximally from the proximal surface 545 of the balloon 540. Similar to the balloon 540, the fiber mesh 560 may have a longitudinal channel extending therethrough from one end of the mesh to the other, the longitudinal axis of the channel through the mesh being coaxial with the longitudinal axis of the channel 543 through the balloon 540. The distal end of the fiber mesh 560 may be attached to the proximal surface 545 of the balloon 540. The channel through the fiber mesh 560 is sized to accommodate the insertion therethrough of the distal sheath 8 of the prosthetic valve delivery device 7.

The fiber mesh 560 may initially be collapsed within a sheath such as the sheath 80 shown in FIG. 2A. To move the fiber mesh 560 from the collapsed condition to the expanded condition, the sheath may be retracted proximally to expose a major portion of the fiber mesh, and the balloon 540 may be inflated from the collapsed condition to the expanded condition. Because the distal end of the fiber mesh 560 is attached to the proximal surface 545 of the balloon 540, the radial expansion of the balloon will draw the fiber mesh into the expanded condition.

Figure 8D:
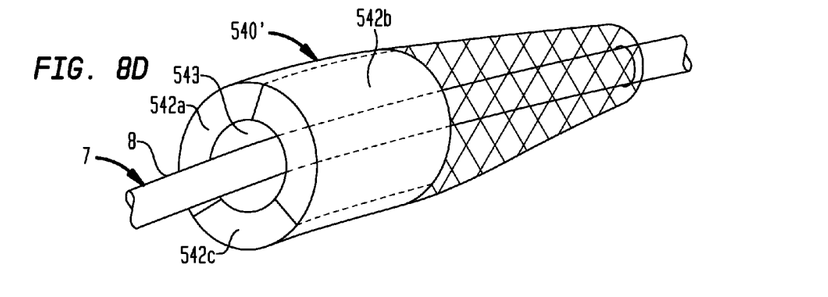
FIG. 8D is a variation of the delivery assistance device of FIG. 8C including a balloon having longitudinal channels.

FIG. 8D illustrates an alternative embodiment of FIG. 8C including a balloon 540' having longitudinal compartments 542a, 542b, and 542c (collectively compartments 542) that can be independently inflated or deflated to desired inflation levels to control the position of the distal sheath extending through the channel 543 of the balloon during deployment of a prosthetic valve. The balloon 540' may have any number of longitudinal compartments 542 other than three, including for example, two, four, or five compartments. In an embodiment having longitudinal compartments 542, a separately controllable inflation lumen may extend from the proximal end of the valve delivery device 7 to each of the compartments.

Although the balloons and mesh materials disclosed herein have been described as having the particular shapes and structures shown in the figures, all of the delivery assistance devices described above may have balloons and mesh materials with any shape and structure. Also, the delivery assistance devices may include one or more balloons having any number of portions, and such portions may or may not be in fluid communication with one another. Furthermore, although the mesh materials in the figures are shown extending proximally from the proximal end of a balloon, there may be a gap between the distal end of the mesh material and the proximal end of the balloon.

Although the delivery assistance devices have been described herein as including a mesh material for preventing calcified particles from entering one or more of the great vessels branching off of the aortic arch, that need not be the case. Rather, each of the delivery assistance devices described herein may be provided without a mesh material. Such delivery assistance devices having a balloon but no mesh material may be used alone or with another delivery assistance device having a mesh material but no balloon.

Although the shafts described herein have been shown as having an elliptical cross-sectional shape, such shape is not critical to the present invention. While the shafts may have any cross-sectional shape, it is preferable that they have a structure that is easier to bend about a first axis of the cross-section than about a second axis transverse to the first axis. Such a bending bias can be achieved even in a shaft having a round cross-sectional shape, for example, by including spaced-apart notches along the shaft in a direction transverse to the longitudinal axis of the shaft.

The shaft is shown having a lumen extending therethrough for insertion of a pigtail catheter, but alternatively, the lumen may be omitted from the shaft. In such a variation, a pigtail catheter or other catheter may be inserted into the aorta separately, such as through the opposite femoral artery or a subclavian artery. The shaft is shown having a lumen extending therethrough for insertion of a pigtail catheter, but alternatively, any other elongated medical apparatus may be inserted through the lumen of the shaft.

The various delivery assistance devices have been described herein in connection with the deployment of a prosthetic aortic valve having a collapsible stent structure, but all of the delivery assistance devices described above may alternatively be used to assist the delivery of other types of aortic valves or to assist the travel of other delivery devices through other portions of the vasculature. For example, the delivery assistance devices may be used to assist implantation of a balloon-expandable prosthetic valve, in which the stent members may be formed of a material that is plastically deformable. In another example, the delivery assistance devices may also be used to assist implantation of conventional collapsible stents or other prosthetic devices that do not contain a valve. Furthermore, the delivery assistance devices may be used to help direct or steer procedural devices to the desired location within a patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An assembly for guiding a medical apparatus within a patient, comprising:
    an elongated shaft having a length direction and a cross-section, the cross-section having a first side and a second side opposite the first side; and
    a balloon affixed to the shaft and movable between a collapsed condition and an expanded condition, the balloon including first and second lobes each having an oblong cross-section in a plane orthogonal to the length direction, the lobes not being in fluid communication with one another, the first lobe in the expanded condition projecting away from the first side of the shaft in a first direction in the plane transverse to the length direction, and the second lobe in the expanded condition projecting away from the second side of the shaft in a second direction in the plane transverse to the length direction, the balloon including a plurality of compartments disposed adjacent to one another in the length direction of the shaft, the balloon including septums that divide adjacent ones of the compartments from one another in the length direction of the shaft.

2. The assembly of claim 1, wherein the shaft includes a lumen extending longitudinally therethrough.

3. The assembly of claim 1, wherein the cross-section of the shaft has an elliptical shape and has a longer dimension extending between the first side and the second side and a shorter dimension extending substantially perpendicular to the longer dimension.

4. The assembly of claim 1, wherein the shaft includes an inflation lumen extending between a proximal end of the shaft and the balloon.

5. The assembly of claim 1, wherein the shaft includes a plurality of inflation lumens and each of the plurality of compartments is in fluid communication with one of the inflation lumens.

6. An assembly for guiding a medical apparatus within a patient, comprising:
    an elongated shaft having a length direction and a cross-section, the cross-section having a first side and a second side opposite the first side;
    a balloon affixed to the shaft and movable between a collapsed condition and an expanded condition, the balloon including first and second lobes each having an oblong cross-section in a direction orthogonal to the length direction, the first lobe in the expanded condition projecting away from the first side of the shaft in a first direction transverse to the length direction, and the second lobe in the expanded condition projecting away from the second side of the shaft in a second direction transverse to the length direction; and
    a mesh material affixed to the shaft and movable between a mesh collapsed condition and a mesh expanded condition, the mesh material projecting away from the shaft in the mesh expanded condition, the mesh material including two wings extending in substantially opposite radial directions from the shaft.

7. The assembly of claim 6, wherein the mesh material is positioned on the shaft proximally of the balloon.

8. The assembly of claim 7, wherein a distal end of the mesh material is attached to a proximal end of the balloon.

9. The assembly of claim 6, wherein the mesh material includes at least one stiffening wire biased to a straight shape.

10. The assembly of claim 6, further comprising an elongated sheath surrounding a portion of the shaft, the sheath being slidable longitudinally along the shaft, wherein the mesh material is collapsed inside the sheath in the mesh collapsed condition.

11. An assembly for guiding a medical apparatus within a patient, comprising:
    an elongated shaft having a length direction and a cross-section, the cross-section having a first side and a second side opposite the first side; and
    a mesh material affixed to the shaft and movable between a collapsed condition and an expanded condition, the mesh material including first and second wings, the first wing in the expanded condition projecting away from the first side of the shaft in a first direction transverse to the length direction, and the second wing in the expanded condition projecting away from the second side of the shaft in a second direction transverse to the length direction, the first and second wings each having an oblong cross-section in a plane orthogonal to the length direction, each wing having a fixed longitudinal edge connected to the shaft and a free longitudinal edge that extends in the length direction of the shaft for at least a portion of the wing.

12. The assembly of claim 11, wherein the mesh material includes at least one stiffening wire biased to a straight shape.

13. The assembly of claim 11, wherein the cross-section of the shaft has an elliptical shape and has a longer dimension extending between the first side and the second side and a shorter dimension extending substantially perpendicular to the longer dimension.

14. The assembly of claim 11, wherein the shaft includes a lumen extending longitudinally therethrough.

15. The assembly of claim 11, further comprising an elongated sheath surrounding a portion of the shaft, the sheath being slidable longitudinally along the shaft, wherein the mesh material is collapsed inside the sheath in the collapsed condition.

* * * * *